(12) United States Patent
Christy

(10) Patent No.: US 6,196,976 B1
(45) Date of Patent: Mar. 6, 2001

(54) TACTILE SENSORY TESTING DEVICE

(76) Inventor: Michael Christy, 2108 Raven Rd., Pleasanton, CA (US) 94566

( * ) Notice: Subject to any disclaimer, the term of this patent is extended or adjusted under 35 U.S.C. 154(b) by 0 days.

(21) Appl. No.: 08/977,002

(22) Filed: Nov. 24, 1997

(51) Int. Cl.[7] .................................................. A61B 19/00
(52) U.S. Cl. .......................................... 600/557; 600/587
(58) Field of Search ..................... 600/553, 557, 600/587

(56) References Cited

U.S. PATENT DOCUMENTS

| | | | |
|---|---|---|---|
| 3,662,744 | * 5/1972 | Low et al. | 600/557 |
| 4,313,446 | 2/1982 | Kanatani | 600/557 |
| 5,275,611 | * 1/1994 | Behl | 600/585 |
| 5,316,011 | 5/1994 | Weinstein et al. | 600/557 |
| 5,381,806 | 1/1995 | Weinstein et al. | 600/557 |
| 5,437,288 | * 8/1995 | Schwartz et al. | 600/585 |
| 5,443,907 | * 8/1995 | Slaikeu et al. | 600/585 |
| 5,492,132 | 2/1996 | Weinstein et al. | 600/557 |
| 5,542,434 | * 8/1996 | Imran et al. | 600/585 |
| 5,562,726 | 10/1996 | Chuter | 623/1 |
| 5,582,619 | * 12/1996 | Ken | 600/585 |
| 5,609,627 | 3/1997 | Goicoechea et al. | 623/1 |
| 5,680,873 | * 10/1997 | Berg et al. | 600/585 |

OTHER PUBLICATIONS

Nitinol . . . The Material of Choice for Safer, More Effective Medical Procedures (FlexMedics Corp., 1989, 2 Pages).*

* cited by examiner

Primary Examiner—Max Hindenburg
Assistant Examiner—Charles Marmor, II
(74) Attorney, Agent, or Firm—Malcolm B. Wittenberg

(57) ABSTRACT

A tactile sensory testing element for determining peripheral nerve sensory function in which commonly used monofilament is exchanged with nitinol, a nickel-titanium alloy which is more dependable in conducting such tests.

1 Claim, 1 Drawing Sheet

TACTILE SENSORY TESTING DEVICE

FIELD OF THE INVENTION

The present invention relates to a device designed to test for a peripheral nerve sensory function. The device includes a filament which is intended to press against a body surface area of a patient and the measure of nerve sensory function is indicated by the patient's perceived recognition of the device as a function of pressure applied to the given surface area.

BACKGROUND OF THE INVENTION

Filament testing for peripheral nerve sensory function has been used more frequently and with renewed interest as the need for screening and monitoring of peripheral nerve sensory function has increased with respect to body therapy. In recent years, it has been shown that filaments are a sensitive monitor means for the testing of the peripheral nerve function of a patient, particularly hand and feet body areas. In the 1800's, the focus of peripheral nerve testing of the hands was on the study of normal physiology and horse hairs were used as filaments to measure only light thresholds of touch recognition.

In the late 1950's, it was determined that a broader range of filament forces were needed than those available with horse hairs to refine the filament method for peripheral nerve testing. Thus, J. Semmes and S. Weinstein designed and developed nylon monofilaments of increasing diameter for peripheral nerve testing with such filaments set at right angles proximate the end of acrylic (Lucite) rods. Such rods, or filament handles, were designed to fit conveniently within a therapist's hand, being approximately the length of a pencil. As noted by reference to the sole figure in the present application as more thoroughly described below, the filament would extend from the rod-like handle at a right angle for perpendicular application to the extremity of a patient. The filament is pressed against the skin of the patient until it bows. Generally, the device is maintained against the extremity of the patient for a specific period of time, for example, for 1.5 seconds, and then removed for 1.5 seconds and then repeated. At that time, the patient is asked whether any sensory perception resulted from the application of the device. If not, the filament would be interchanged by one of a larger diameter so that increased pressure would be required prior to causing the filament to once again bow.

The Semmes-Weinstein monofilament testing devices have become the standard means for repeatable testing and measurement of the threshold of cutaneous sensory perception. Through the 20-unit series of test devices, a trained hand therapist or health care examiner can distinguish in a patient between light touch, diminished light touch, diminished protective sensation, loss of protective sensation and deep pressure sensation. A series of nylon monofilaments (of uniformed 38 mm length) are sized and numbered to correspond to Log (10×force in mg) of force. The lowest force in the series is 4 mg and the highest force is 447 grams. The monofilaments (of constant length but of increasing diameters) are designed to bend when a specific value of force is reached and such design provides unique control of, and credibility to, the Semmes-Weinstein sensory test method. Thus, the series of Semmes-Weinstein test devices provides an accurate method by which diminishing and returning sensation of a patient's body surfaces and extremities can be evaluated and allows the health care examiner to predict and interpret the patient's levels of nerve function and sensibility.

Virtually all Semmes-Weinstein monofilament test devices employ nylon as the force applying element. These are usually provided as a set of five units having selected sensory level designations of 2.83, 3.61, 4.31, 4.56 and 6.65. It has been observed, however, that nylon monofilament suffers from certain drawbacks which reduces the overall efficacy of the cutaneous sensory perception measuring device. Simply put, it is critical in using the Semmes-Weinstein monofilament testing instrument to be constant and predictable in the amount of force applied to the specific body surface area of the patient as it relates to the sensory level designation of the monofilament segment being employed. It must be remembered that the sensory perception of the patient is measured by applying sufficient force to the preselected body area so that the monofilament segment bows by the application of sufficient orthogonal pressure. The sensory level designations relate to contrasting monofilament diameters so that bowing occurs at certain preselected pressure levels.

Unfortunately, notwithstanding its universal acceptance, nylon proves to be a less than ideal choice for use as a testing instrument. For example, as noted above, the force delivered by a monofilament segment is the function of the diameter of the filament and its length. When force is applied to the filament, it is distributed along its entire length. Bending occurs when the monofilament column begins to elongate on the side of the filament and compresses on the opposite side. At the point of initial bending the maximum moment of force is delivered. However, when additional force is applied, it is not uncommon to cause the filament to "kink." When this happens, the bending force cannot build along the entire length of the filament but, instead, the force "collects" at the kink. The bend that results focusses at the kink such that the force to elongate one side of the kink and compress the opposite side is reduced. Not surprisingly, the dynamics of the bending moment of the monofilament are dramatically changed noting that efforts to straighten the kink will not resolve the loss in force to bending. As such, once a kink has occurred, the standard predictable moment of force required to form a uniform bend in order to make a peripheral nerve function determination is lost. Nylon is, unfortunately, quite susceptible to kinking.

In addition to the above, nylon, due to the very nature of its molecular structure, lacks the necessary consistent force to cause bending from monofilament to monofilament. As such, nylon monofilament allows a therapist to make gross measurements relating to cutaneous sensory perception of a patient's body areas but finely tuning such measurements is not practical. There are several reasons why nylon has proven to be less than ideal as a measuring device. It has been noted that nylon is sensitive to climactic conditions such as ambient temperature and humidity. Fairly dramatic differences in bending force are measured when such climactic conditions are altered. Further, nylon requires a relaxation period in order to operate properly. It has been observed that the bending force of a nylon monofilament remains constant after use until the monofilament has been employed for five to ten consecutive applications, at which time, the monofilament requires up to six hours to recover its original flexural modulus.

It is thus an object of the present invention to provide a Semmes-Weinstein type of cutaneous sensory perception device wherein the nylon monofilament has been replaced by a material which enables the device to work in a more predictable and thus acceptable manner.

This and further objects will be more readily appreciated when considering the following drawings and appended claims.

SUMMARY OF THE INVENTION

The present invention involves a device for testing for peripheral nerve sensory function in a human patient. The device comprises a handle and extending from the handle a length of filament for contacting body surface areas of the patient. Testing is accomplished by pressing the filament against body surface areas until the filament bends. Sensory perception is determined by eliciting the patient's reaction to the application of the filament. The present invention represents an improvement over prior devices of this type by constructing the filament of nitinol.

DETAILED DESCRIPTION OF THE INVENTION

Figure 1:
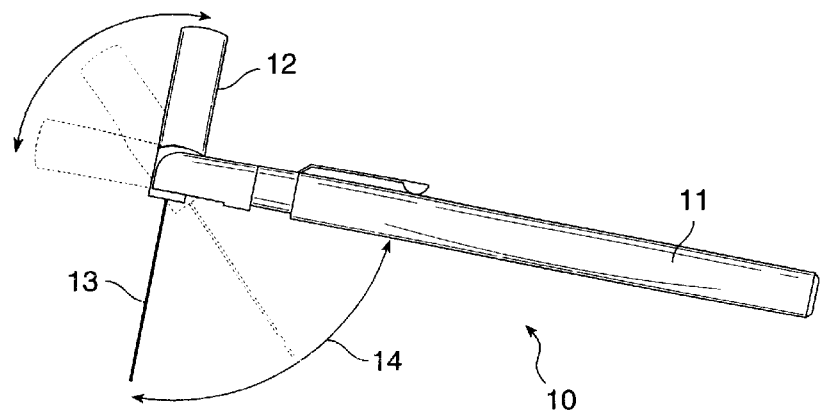
FIG. 1 is a side plan view of a Semmes-Weinstein monofilament testing device of the present invention.
Figure 2:
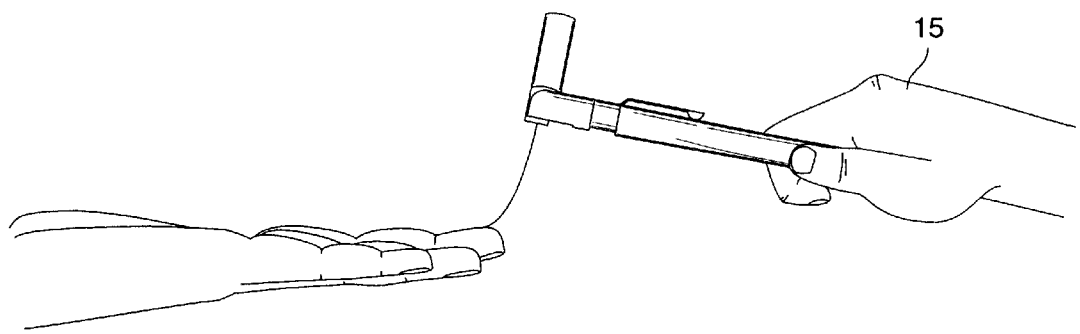
FIG. 2 is a side perspective view of the device of FIG. 1 being employed to measure sensory perception of a patient's finger.

Reference is made to FIG. 1 which illustrates a typical Semmes-Weinstein test unit 10. This device is provided with a handle 11 sized to conveniently fit within hand 15 of a therapist (FIG. 2). When not in use, head 12 swivels as depicted by arrow 14 to be co-extensive with the longitudinal axis of handle 11. During storage, filament 13 swings within handle 11 and resides in a groove (not shown) within handle 11 for its protection. In use, end unit 12 swivels to a position perpendicular to handle 11, the device taking on the orientation as shown in FIG. 1.

FIG. 2 shows the use of the device of the present invention. A therapist grasps handle 11 and applies the device to a finger of hand 16 of a patient. Force is applied until filament 13 bows as shown. If the pressure required to cause bowing is consistent from filament to filament, accurate determinations can be made as the amount of force necessary to cause a sensory perception by the patient.

In order to provide a device dramatically improved over similar devices of the prior art employing nylon monofilament, the present invention is intended to employ filament segments 13 composed of nitinol. Nitinol is a well-known nickel-titanium alloy wire which can be configured in various diameters in order to be direct replacements for the nylon units of the prior art. It was determined that nitinol dramatically improves the kink resistance of the filament and, in fact, its kink resistance is superior to that even of steel. Nitinol also exhibits excellent resistance to flex fatigue while its overall reproducibility of measurements is dramatically superior to nylon. Finally, nitinol is much less sensitive to temperature or humidity fluctuations than nylon.

Nitinol filaments can be directly employed by inserting suitable replacement filaments 13 within prior art handles 11. As is the case with nylon, it is contemplated that such filaments remain of constant length while filaments within a given series differ from each other by differing diameters.

Figure 3:
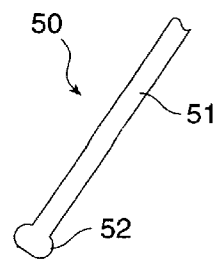
FIG. 3 is a perspective view of a monofilament segment illustrating a preferred embodiment of the present invention.

As a preferred embodiment, reference is made to FIG. 3 which shows a modification of the nitinol filament of the present invention. As background, it is noted that the "footprint" of a nitinol monofilament is about 20% of a corresponding nylon version while exhibiting the same pressure/bending characteristics. As a consequence, for the same force, higher pressure will be generated at skin contact using the filament of the present invention. It is reasonable to expect a higher sensitivity to this force or pressure which, of course, undermines the clinical basis for using a material other than nylon.

In order to correct for the observation of higher pressure, it is proposed that the "footprint" of the nitinol filament 50 be expanded by creating a region 52 at the contact end of shaft 51 to, for example, emulate the cross-section of the nitinol filament if composed of nylon. This can be done a number of ways such as by laser or arc melting of the end of the nitinol filament or by employing a potting material such as a plastic or metal throughout the length of the wire or only on the end of the filament intended to contact the human patient during sensory testing. Region 52 can take on the shape of a bead, cylinder, sphere or tear drop, the exact shape being less important than the fact that region 52 is of expanded area from the filament shaft 51.

It was further noted that as the diameter of the nitinol filament is increased, its ability to bend without kinking diminishes with a decreasing length to diameter (l/d) ratio. At the 300–400 gram force delivery range, the target 1.5 inch length during an abusive application technique may result in a curvature of the wire being set. To lessen this possibility, it is proposed that the length of the nitinol filament, as a preferred embodiment, be in the range of approximately 1.75 to 2.5 inches in order to improve the l/d ratio. Further, although the length of the filament is typically 1.50 inches, with thinner diameter, one can use nitinol filaments at lengths as low as ½ inch while adjusting the filament's footprint as noted above to deliver targeted pressure.

I claim:

1. In a device for testing for peripheral nerve sensory function in a human patient, said device comprising a handle and extending from said handle, a length of filament for contacting body surface areas of said patient by pressing said filament against said body surface until said filament bends in determining if said patient feels said filament, said filament being constructed of nitinol and wherein said filament is characterized as having a length and cross-section, and wherein said filament is provided with a cross-section of expanded size on an end of the filament which is intended to contact the human patient during sensory testing, the improvement comprising an expanded cross-section formed by coating and potting a portion of said filament.

* * * * *